United States Patent [19]
Kroll et al.

[11] Patent Number: 5,325,870
[45] Date of Patent: Jul. 5, 1994

[54] MULTIPLEXED DEFIBRILLATION ELECTRODE APPARATUS

[75] Inventors: Mark W. Kroll, Minnetonka; Theodore P. Adams, Edina; Joseph S. Perttu, Chanhassen; Charles Supino, Arden Hills, all of Minn.

[73] Assignee: Angeion Corporation, Plymouth, Minn.

[21] Appl. No.: 991,132

[22] Filed: Dec. 16, 1992

[51] Int. Cl.⁵ .............................................. A61N 1/04
[52] U.S. Cl. .................................................... 607/122
[58] Field of Search ........................ 176/784–788, 176/419.0 PG

[56] References Cited

U.S. PATENT DOCUMENTS

| | | | |
|---|---|---|---|
| 3,405,715 | 10/1968 | Hagfors | 128/784 |
| 3,942,536 | 3/1976 | Mirewski et al. | 128/786 |
| 3,968,802 | 7/1976 | Bollis | 128/419.0 PG |
| 4,289,134 | 9/1981 | Bernstein | 128/419.0 PG |
| 4,320,763 | 3/1982 | Money | 128/419.0 PG |
| 4,355,646 | 10/1982 | Kallok et al. | 128/786 |
| 4,628,934 | 12/1986 | Dorf et al. | 128/786 |
| 4,745,923 | 5/1988 | Winstrom | 128/419.0 PG |

*Primary Examiner*—William E. Kamm
*Attorney, Agent, or Firm*—Joel D. Skinner

[57] ABSTRACT

A defibrillation electrode apparatus which provides defibrillating, pacing, and sensing functions with the use of fewer conductors. Conductor requirements are minimized by solid-state multiplexing that is accomplished at the distal end of the apparatus.

17 Claims, 3 Drawing Sheets

MULTIPLEXED DEFIBRILLATION ELECTRODE APPARATUS

BACKGROUND OF THE INVENTION

This invention relates to electromedical apparatus and particularly to implantable, transvenous catheter-type electrode devices. The apparatus of this invention is particularly useful for cardiac defibrillation in conjunction with an implantable cardioverter/defibrillator (ICD).

Defibrillating the human heart is accomplished by applying an electrical waveform to the cardiac muscle with appropriate electrodes, causing the cessation of the rapid uncoordinated contractions of the heart (fibrillation), and a restoration of normal beating of the heart. In the past, various electrode devices and/or methods have been used and proposed for defibrillation. However, these devices are generally complex, difficult to construct and utilize, and are inefficient to use.

A well-functioning, unitary defibrillation electrode catheter should accomplish three functions. The first is that it should provide a high surface area, low impedance current path for the high energy defibrillation pulse, which may be up to 750 volts. Secondly, it should provide a pair of pacing electrodes which have a small surface area to also deliver a low energy pacing pulse of approximately 5 volts. The small surface area is desired so that pacing may be accomplished at a high local current density resulting in lower overall energy usage. The low energy usage of the pacing function is of concern since pacing may be required to proceed uninterrupted for many years. The third function of the defibrillation electrode is sensing. A pair of small surface area electrodes, commonly referred to in the art as a bipolar pair, is used to sense a local differential voltage representing the electrogram in the ventricle of the heart. Ideally, the bipolar pair of electrodes additionally serve as pacing electrodes.

Besides providing for the above three basic functions, the unitary electrode lead must also prevent possible detrimental interactions. Thus, the electrode lead must keep the pacing pulse from being shunted by the defibrillation electrodes. The electrode catheter must also keep the sensed electrocardiographic signals from being corrupted by signals from the large defibrillation electrodes. Finally, the electrode lead must keep high defibrillation currents from flowing through the smaller pacing and sensing electrodes which could polarize them and interfere with their ability to properly sense the electrogram after a defibrillation pulse.

The current state of the art includes electrode apparatus having four separate electrodes, distally disposed, each linked to a separate conductor or lead, and each of which runs the length of the apparatus to a proximal connection end. Both co-axial and multi-lumen configurations of such leads exist. However, all of such four lead configurations present limitations in terms of minimizing apparatus diameter or profile. And, since such large apparatus are used intravascularly in human beings, this limitation is critical.

Despite the need for a electrode apparatus which overcomes the limitations and problems of the prior art, none insofar as is known has been proposed or developed. Accordingly, it is an object of the present invention to provide an apparatus which overcomes the limitations and short comings of the prior art. Particularly, it is an object of the present invention to provide an improved transvenous alefibrillation catheter apparatus which is safe, reliable, and inexpensive to manufacture. A further object of this invention is to provide a low profile, minimal diameter electrode apparatus. Yet another object of this invention is to provide a full function defibrillation electrode apparatus which utilizes not more than three, and preferably two conductive leads. A final object of this invention is to provide and electrode apparatus in which lead conductor requirements are minimized by solid state multiplexing which is accomplished at the distal end of the apparatus.

SUMMARY OF THE INVENTION

The present invention provides a transvenous defibrillation catheter apparatus, comprising an insulative body structure, four electrode members disposed on the body structure for electrical communication with the exterior environment, and not more than three conductive lead members. Each lead member is communicatively connected to at least one electrode member and extending therefrom to a predetermined point on the body structure.

A particular embodiment of the invention provides a low diameter, transvenous defibrillation catheter apparatus, comprising an elongated insulative body structure having a distal and proximal end and four electrode members disposed on the body structure for electrical communication with the human body. The four electrode members include a positive defibrillation electrode, a negative defibrillation electrode, a positive pace/sense electrode and a negative pace/sense electrode. A first lead is connected to the positive defibrillation lead, a second lead is connected to the positive pace/sense electrode, and a third lead is connected to the negative defibrillation lead and to the positive pace/sense electrode. Each lead extends from its respective electrode to the proximal end of the body structure. This embodiment further comprises first rectifier means connected between the first lead and the negative defibrillation electrode, and second rectifier means connected between the first lead and the negative pace/sense electrode. Both rectifier means are preferably distally disposed.

Other embodiments of the invention provide a low diameter, transvenous defibrillation catheter apparatus, comprising an elongated insulative body structure having a distal and a proximal end and four electrode members disposed on the body structure for electrical communication with the human body. The four electrode members include a positive defibrillation electrode, a negative defibrillation electrode, a positive pace/sense electrode and a negative pace/sense electrode. A first lead is connected to the positive defibrillation electrode and to the negative pace/sense electrode. A second lead is connected to the negative defibrillation electrode and to the positive pace/sense electrode. Each lead extends from its respective electrode to the proximal end of the body structure. These embodiments further comprise a first rectifier means connected between first lead and the positive defibrillation electrode, second rectifier means or first current limitation means connected between the first lead and the negative pace/sense electrode, third rectifier means connected between the second lead and the negative defibrillation electrode, and fourth rectifier means or second current limitation means connected between the second lead and the positive pace/sense electrode. Each rectifier or current limitation means is preferably distally disposed.

These and other benefits of this invention will become clear from the following description by reference to the drawings.

DESCRIPTION OF THE PREFERRED EMBODIMENT

Implantable defibrillator or cardioverter/defibrillator apparatus (not shown) are linked to an electrode apparatus which conduct current from the device to the human heart. One type of electrode apparatus a catheter type apparatus having a pair of large surface area defibrillation electrode coils and a pair of small surface area pace/sense electrode bands, is threaded into the heart chambers through the patient's veins. Such an apparatus is known as transvenous electrode apparatus. One coil-type defibrillation electrode is typically disposed just above the heart in the right atrium (RA) location and the other is disposed in the right ventricular apex (RVA). The band-type pace/sense electrodes are oriented in the right ventricle.

The functional part of both of the defibrillation electrodes is either a ribbon or coil of conductive wire wrapped around a flexible polymer. A typical coil diameter is 2-3 mm., and typical lengths of the coil electrode are 4 to 12 cm. The functional part of the pace/sense electrodes is often a solid band of conductive material. The lead conductors of the catheter structure enter from the left and are attached to the electrode coils and bands at one or both ends thereof. This provides for a low resistance connection between the lead conductor and the electrode coil or band.

Figure 1:
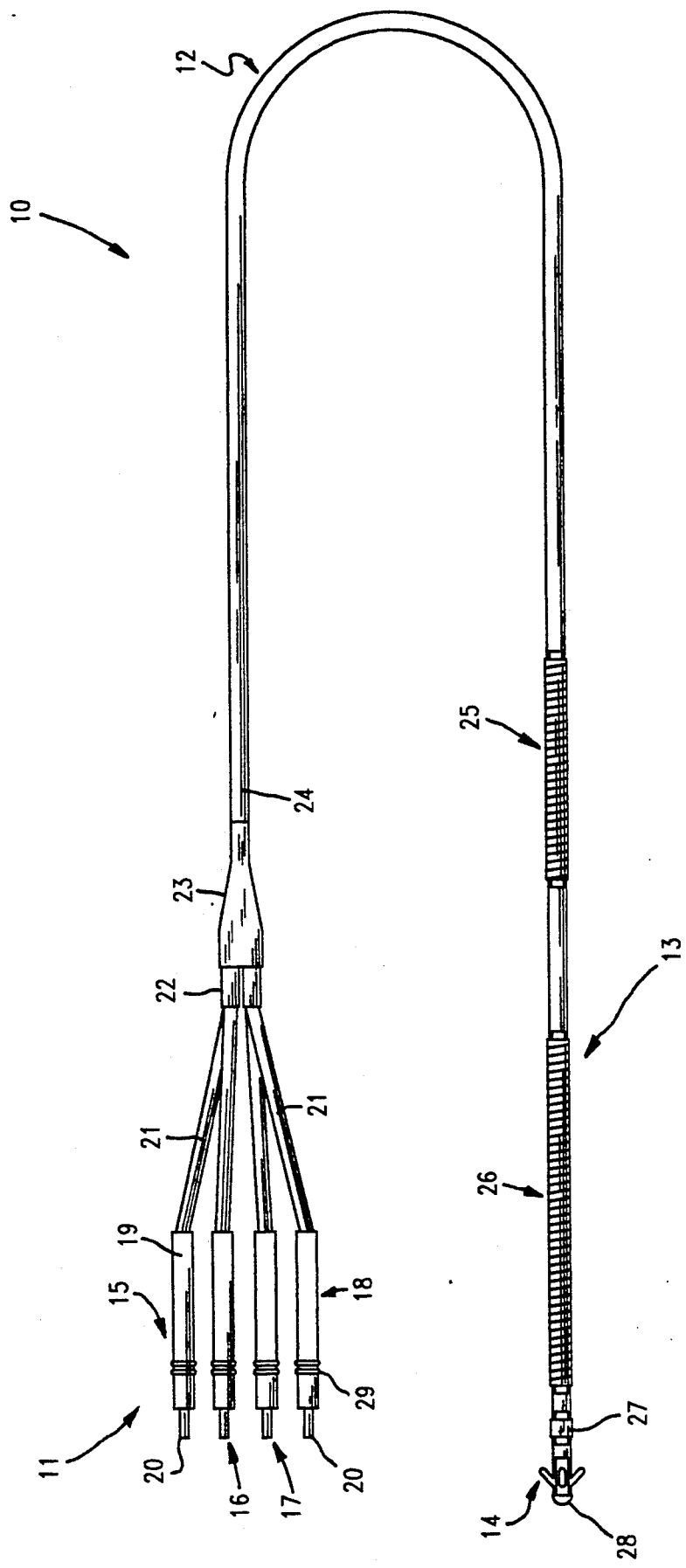
FIG. 1 is a perspective view of a prior art catheter-type defibrillation electrode apparatus.
Figure 2:
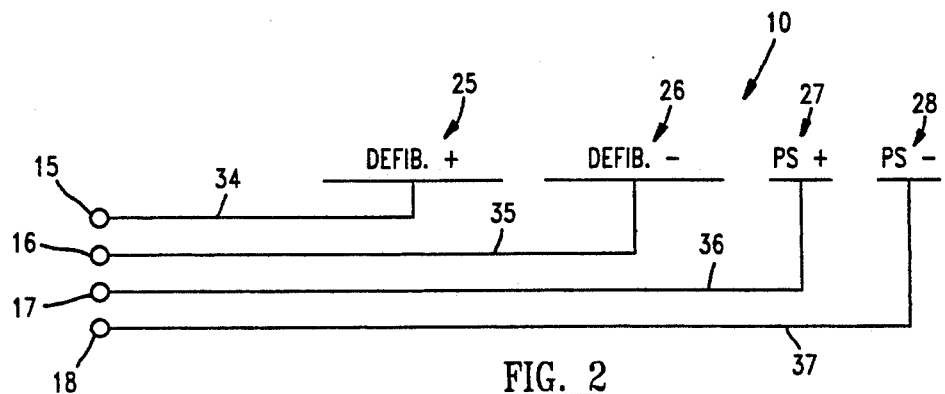
FIG. 2 is a schematic diagram of the prior art circuitry of the apparatus of FIG. 1.

Referring to FIG. 1, the typical prior art defibrillation catheter 10 has a thin, elongated tubular structure with a connection end 11 for mating with an implantable cardiac defibrillator apparatus (not shown), a cable 12 extending a predetermined length from the connection end 11, and an electrode end 13 disposed at the other end of the cable 12. The electrode end 13 has a predetermined length and terminates in an anchor structure 14 which lodges in cardiac tissue on the interior of the patient's heart.

The connection end 11 is communicatively connectible to the ICD and is shown to have four (4) terminal leads, 15, 16, 17 and 18. Each terminal lead 15-18 comprises a lead plug end 19 having plug end tip 20, an insulated lead conductor 21, and a strain relief sheath 22. All of the terminal leads 15-18 run into a lead collector 23 which interfaces the catheter cable 12.

The electrode end 13 is shown to have four (4) electrodes 25, 26, 27 and 28, spaced at predetermined intervals and corresponding to the leads 15-18. In a typical device 10 application, electrode 25 is a proximal defibrillation electrode, electrode 26 is a distal defibrillation electrode, electrode 27 is a proximal pace/sense electrode, and electrode 28 is a distal pace/sense electrode.

The spacing of the defibrillation electrodes 25 and 26 is a function of the structure and dimensions of the human heart and the prescribed location of the electrodes 25 and 26 therein, typically at the connection of the superior vena cava to the heart and at the left ventricle. Additionally, the length and outer surface area of the electrodes 25 and 26 is selected to maximize current distribution to the patient's heart tissue.

Referring also to FIG. the cable 12 communicatively connects the four leads 15-18 of the connection end 11 with the four electrodes 25-28 of the electrode end 13. In the circuit schematic, the two defibrillation electrodes are referred to as (alefib+) and (defib−) and the two pace/sense electrodes are referred to as (ps+) and (ps−). The cable 12 may have either a multi-lumen or coaxial design with four (4) lead conductors 34, 35, 36 and 37. Regardless of design, each lead conductor 34-37 is surrounded by at least one inner insulator. Additionally, an outer insulator 24 surrounds the entire group of leads. The leads 34-37 are constructed of a conductor such as a solid metallic wire, a plurality of twisted strands of wire or a single coiled wire. The insulators are constructed of a non-conductive polymeric substance, such as polyurethane. Two conductors communicate with the defibrillation electrodes and two communicate with the pace/sense electrodes. It should be noted that there is no detriment in the pacing and sensing functions being performed by the same electrodes. This is because pacing is not performed at the same time as sensing, and the five volt pacing pulse does not generate high, potentially polarizing currents.

The problem with prior art catheter leads having the above-described structure is that, due to their 4-lead structure, they have a relatively large diameter. A typical prior art catheter electrode device has a diameter of approximately 4 mm, which is relatively difficult to insert through a patient's veins. In addition, high voltage (750 volt) defibrillation pulses stress the catheter insulation. Thus, a greater number of conductors yields a greater potential for catheter failure.

Figure 3:
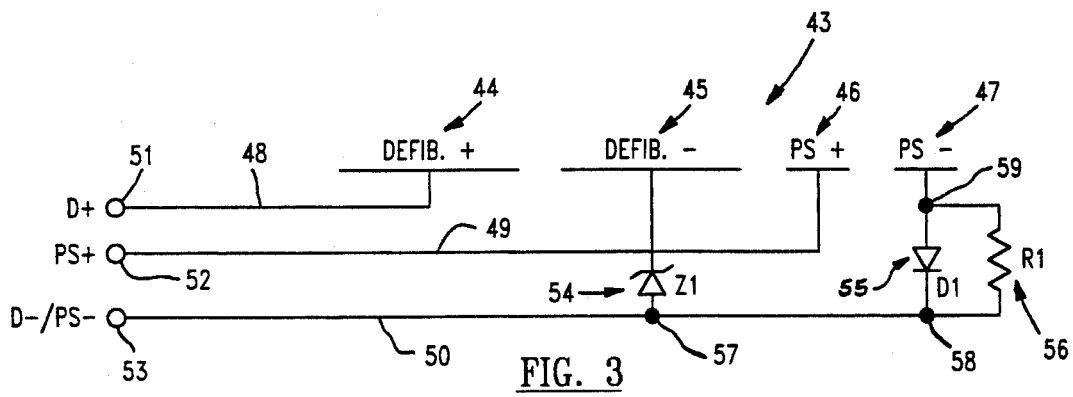
FIG. 3 is a schematic diagram of circuitry of the present invention.

The present invention utilizes simple, reliable, and common electronic components placed at the end of the catheter to allow multiple uses of the catheter conductors. Referring to FIG. 3, the electrode catheter 43 of the present invention comprises positive and negative defibrillation electrodes 44 and 45, positive and negative pace/sense electrodes 46 and 47, and conductive first, second and third leads 48, 49 and 50 each shown terminating in an input/output node 51, 52 and 53, respectively. The first, second and third nodes 51-53 are configured in a suitable manner, as for example shown at terminal end 11 in FIG. 1. First lead 48 directly connects the defibrillation positive electrode 44 to the first or defibrillation positive connection node 51. Similarly, second lead 49 directly connects the pace/sense positive electrode 46 to the second or pace/sense positive node 52. The third lead 50 couples both the defibrillation negative electrode 45 and the pace/sense negative electrode 47 to the third or defibrillation negative-/pace/sense negative node 53.

A zener diode 54 is disposed between node 57 on lead 50 and the defibrillation negative electrode 45. The anode of zener diode 54 is disposed toward node 53, while its cathode is disposed toward electrode 45. A diode 55 and resistor 56 are disposed between input/output node 53 and pace/sense negative electrode 47, each being further connected to nodes 58 and 59 so that they are in a parallel configuration with respect to each other. The anode of diode 55 is disposed on the electrode 47 side while the cathode is disposed on the input/output node 53 side.

This embodiment of the apparatus 43 of the invention has isolated conductors for the (defib+) and (ps+) electrodes 44 and 46. However, the (defib−) and (ps−) electrodes 45 and 47 now share a lead conductor 50 labeled as d−/ps−. To prevent various potential interferences from occurring, three electronic components are added near the electrodes. Zener diode (Z1) 54 is connected from the common conductor 50 to the (defib−) electrode 45. Zener diodes conduct electricity in only one direction. However, after a predetermined amount of voltage exists in a reverse direction, the diode 54 will "break down" and begin conducting in that reverse direction. Preferably, Zener diode 54 has a "break down" voltage of approximately 8 volts. The common conductor 50 is also connected to the (ps−) electrode 47 through diode (D1) 55 and resistor (R1) 56. The resistor 56 limits current and the diode 55 limits the flow of currents to one direction.

In a sensing mode, the sensed electrocardiographic signal passes through the (ps−) electrode 47 through resistor 56 and through the common conductor 50. Because the millivolt level electrocardiographic signal is insufficient to turn on the Zener diode 54, even in the forward direction, there is no shunting by the (defib−) electrode 45 which is also connected to conductor 50. Pacing is accomplished by having the pacing current flow through diode 55 and then through the common conductor 50. Any potential shunting of the pacing signal through the (defib−) electrode 45 coil is prevented as the 5 volt pacing pulse is insufficient to break down the 8 volt rated Zener diode 54.

In a defibrillation mode, the high defibrillation current is carried through the Zener diode 54. The loss of approximately 8 volts experienced at the diode 54 is insignificant relative to the 750 volt maximum pulse used in defibrillation. The defibrillation current flows from the (defib+) electrode 44 to the (defib−) electrode 45 and then through Zener diode 54. A small amount of shunting may occur through the (ps−) electrode 47 and thence through the diode D1 55. However, this shunting phenomena is minimized due to the fact that the (ps−) electrode 47 is disposed beyond the (defib−) electrode 45, and far away from the (defib+) electrode 44. Hence, it is "downstream" and unlikely to carry any significant currents. This circuit scheme largely meets the requirements of the ideal unitary lead discussed above, although there may be some conduction through the (ps−) electrode 47 which may potentially yield a small amount of polarization at the electrode 47.

Figure 4:
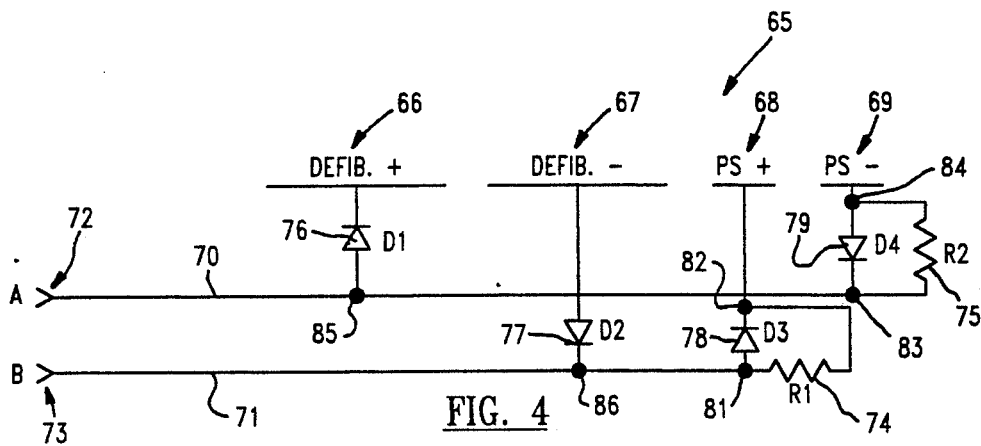
FIG. 4 is a schematic diagram of an alternative embodiment of the invention.

Referring to FIG. 4, an alternative embodiment of the electrode catheter 65 comprises positive and negative defibrillation electrodes 66 and 67, positive and negative pace/sense electrodes 68 and 69, and first and second conductive leads 70 and 71, each lead terminating in an input/output node 72(A) and 73(B), respectively. First lead 70 connects both the defibrillation positive electrode 66 and the pace/sense negative electrode 69 to the A node 72. The second lead 71 connects both the defibrillation negative electrode 67 and the pace/sense electrode 68 to the B node 73.

A first diode 76 is disposed between node 85 on lead 70 and the defibrillation positive electrode 66. The anode of the diode 76 is disposed toward the A node 72 and the cathode toward the electrode 66. A second diode 77 is disposed between node 86 on lead 71 and the defibrillation negative electrode 67. A third diode 78 and first resistor 74 are disposed between the pace/sense positive electrode 68 and B node 73, each being further connected to nodes 81 and 82. The anode of the diode 78 is disposed toward the B node 73. A fourth diode 79 and second resistor 75 are disposed between the pace/sense negative electrode 69 and the A node 72, each being further connected to nodes 83 and 84. The anode of the diode 79 is disposed on the electrode 69 side. The anode of the diode 77 is disposed on the electrode 67 side.

This is an improved embodiment of the catheter 65 which allows the use of only two conductors 70 and 71 in the catheter structure by the addition of two more diodes and one more resistor. In this embodiment, the top common conductor is designated the "A" conductor 70 and the lower common conductor the "B" conductor 71. In a sensing mode, one sensing signal travels from the (ps+) electrode 68 through resistor 74, then through the "B" conductor 71. The other sensing signal runs from the (ps−) electrode 69 through the resistor 75, and then through the "A" conductor 70. In neither case are these sensing signals shunted by the (defib +/−) electrodes 66 and 67 as they are millivolt level signals and do not turn on the diodes 76 or 77. Pacing is accomplished by driving line A 70 negative and line B 71 positive. This back-biases the defibrillation diodes 76 and 77 and hence they do not conduct. However, this pacing signal easily conducts through diodes 78 and 79, thus delivering a normal pacing pulse through pace/sense positive and negative electrodes 68 and 69.

In a defibrillation mode, a defibrillation current is delivered through the pathway of conductor A 70, through diode 76 through (defib+) electrode 66, through the patient's heart, thence to (defib−) electrode 67, through diode 77 and back through conductor B 71. This circuit does not exhibit the small shunting phenomena as occurs with the circuit shown in FIG. because the potential parasitic return path is non-existent. The diode 79 is back biased as well as the diode 78.

One limitation of the electrode embodiment of FIG. 4 is that it is unable to deliver a multiple polarity or "biphasic" defibrillation pulse. Recent studies have shown that a biphasic defibrillation pulse has lower energy requirements for defibrillating the heart than does the classical monophasic pulse. The biphasic pulse is generated by discharging a capacitor into the heart, through appropriate electrodes, for several milliseconds and then reversing the connection and generating a reverse voltage across the electrodes. The circuitry 65 shown in FIG. 4 will not tolerate a biphasic pulse as the second (or reversed) phase would back-bias the diodes 76 and 77. Thus, a catheter having this circuitry 65 would not conduct the second phase of the biphasic pulse.

Figure 5:
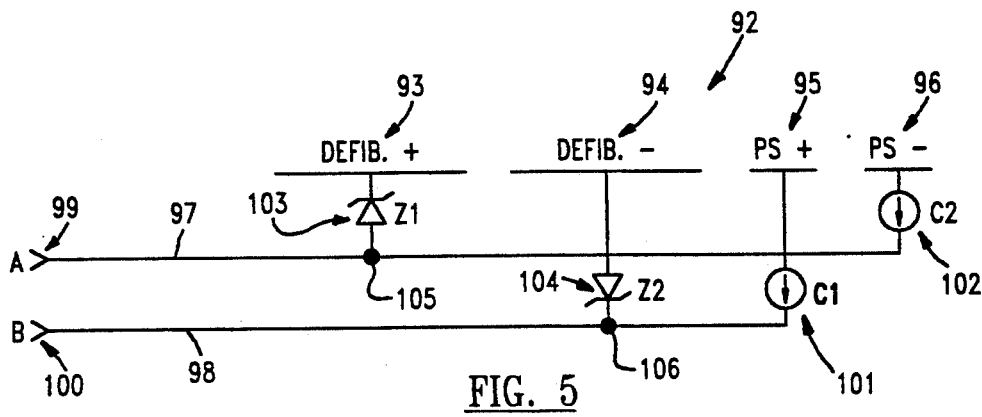
FIG. 5 is a schematic diagram of an alternative embodiment of the invention.
Figure 6:
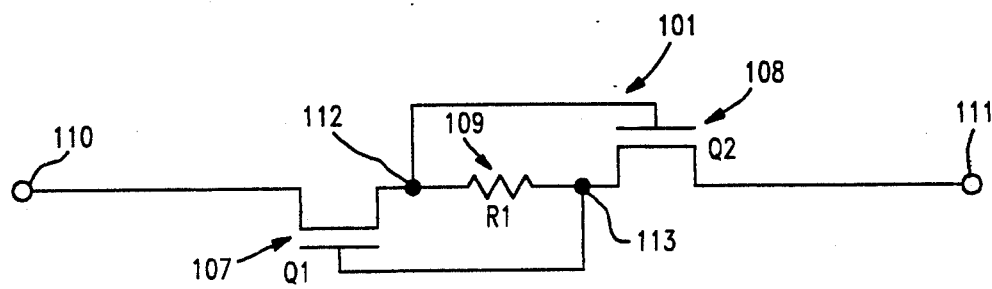
FIG. 6 is a schematic diagram of a current limiting circuit utilized in the circuit of FIG. 5.

An alternative embodiment, shown in FIGS. 5 and 6 does allow the usage of a biphasic pulse. The electrode catheter 92 comprises positive and negative alefibrillation electrodes 93 and 94, positive and negative pace/sense electrodes 95 and 96, and first and second conductive leads 97 and 98. Each lead 97 and 98 terminates in an input/output node 99(A) and 100(B). The first lead 97 connects both the defibrillation positive electrode 93 and the pace/sense positive electrode 96 to the A node 99. The second lead 98 couples both the defibrillation negative electrode 94 and the pace/sense positive electrode 95 to the B node 100.

A zener diode 103 is connected between the defibrillation positive electrode 93 and node 105 on lead 97. The anode of the diode 103 is disposed on the node 99 side while the cathode is disposed on the electrode 93 side. A second zener diode 104 is disposed between the defibrillation negative electrode 94 and node 106 on lead 98. The anode of the diode 104 is disposed toward the electrode 94 and the cathode is disposed toward the B node 100. A first current limiting circuit 101 is disposed between pace/sense positive electrode 95 and node 106 of lead 98. A second current limiting circuit 102 is disposed between the pace/sense negative electrode 96 and node 105 of lead 97.

Referring to FIG. 6, the first current limiter 101 is shown to comprise a pair of N-channel depletion mode field effect transistors 107 and 108 and a resistor 109 which are disposed between first and second input/output nodes 110 and 111. The source and drain of each transistor 107 and 108 are connected in series with each other between nodes 110 and 111. The resistor 109 is connected in series between the two transistors 107 and 108. Additionally, the gate of transistor 107 is shown to be connected to the far side of resistor 109, at node 113. And, the gate of transistor 108 is connected to the far side of resistor 109, relative to transistor 108, at node 112.

The biphasic pulse tolerant approach of this circuitry depends on the current limiter circuit section shown in FIG. 6. The two field effect transistors 107 and 108 have gates which are connected across the current dropping resistor 109. When a high current is passed through such a circuit 101 or 102, a negative voltage is generated across the transistor 107 or 108 gate which suffices to turn off the appropriate transistor. In this way, the circuit 101 or 102 limits the current through itself. At low currents the circuit 101 or 102 simply behaves as if it merely comprised the resistor 109. With appropriate choices of components the circuit 101 or 102 acts as a 200 ohm resistor which is able to perform sensing and pacing functions yet limit the current to merely several milliamps with the application of a defibrillation pulse.

In the electrode circuitry 92 the current limiters 101 and 102 take place of the diode-resistor combinations of the circuitry 65 shown in FIG. 4. These current limiters 101 and 102 prevent the flow of defibrillation level currents through (ps+) and (ps−) electrodes 95 and 96. However they do not interfere with normal pacing and sensing functions of the circuitry 92. The diodes for defibrillation are now replaced by Zener diodes 103 and 104 which have breakdown voltages in excess of the pacing voltage. In a typical application, pacing is done at 5 volts and the breakdown voltage of the Zener diodes 103 and 104 is 8 volts. For defibrillation, the current flows from conductor A 97 forward through Zener diode 103 and into the (defib+) electrode 93. Defibrillation current then flows to the (defib−) electrode 92 and through Zener diode 104 in a forward direction and back through conductor B 98. For a biphasic pulse, the voltage will be reversed between conductors B and A 98 and 97. The defibrillation current now flows from connector B 100 through Zener diode 104 (since there is an excess of voltage necessary to break down Zener diode 104) then through (defib−) and (defib+) electrodes 94 and 93 respectively. Again, 8 volts is used in breaking down Zener diode 103 and the current then flows back through conductor A 97. The Zener diodes 103 and 104 are not broken down by the 5 volt pacing pulse and hence that energy is not shunted through the defibrillation electrodes 93 and 94. During pacing, conductor A 97 is brought negative and connector B 98 is at a positive voltage relative to A. However, this positive voltage is typically at 5 volts and insufficient to break down Zener diode 103 and hence there is no shunting through the (defib+) electrode 93.

Figure 7:
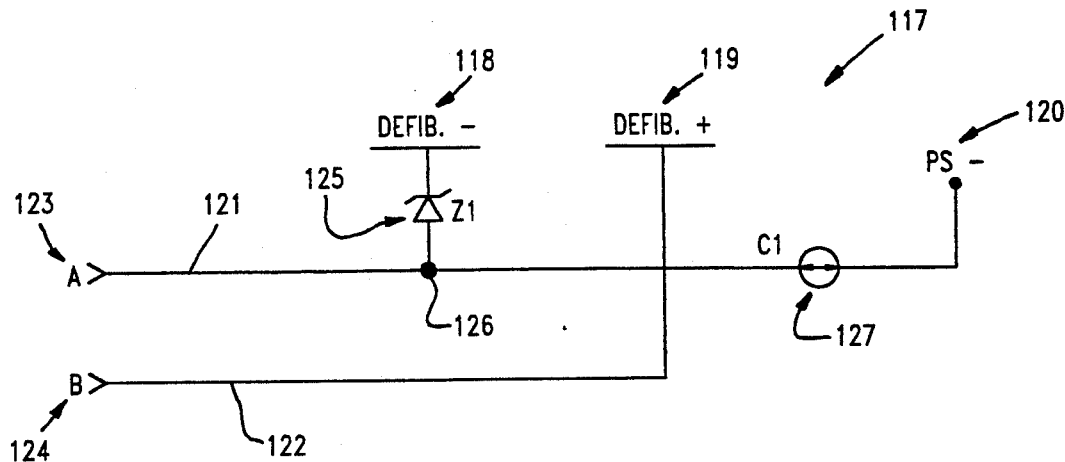
FIG. 7 is a schematic diagram of an alternative embodiment of the invention.

Referring to FIG. 7, an alternative embodiment of the electrode catheter 117 comprises positive and negative defibrillation electrodes 119 and 118, a pace/sense reference 120, and first and second conductive leads 121 and 122, each lead terminating in an input/output node 123(A) and 124(B), respectively. First lead 123 connects both the defibrillation negative electrode 118 and the pace/sense reference 120 to the A node 123. The second lead 122 connects the defibrillation positive electrode 119 to the B node 124.

A diode 125 is disposed between node 126 on lead 121 and the defibrillation negative electrode 118. The anode of the diode 125 is disposed toward the A node 123 and the cathode toward the electrode 118. A current limiter 127 is disposed between the pace/sense reference 120 and the node 126 on lead 121.

This embodiment of the catheter 117 allows the use of only two conductors 121 and 122 in a two electrode catheter structure which utilizes a reference for pace/sense function instead of an extra pair of electrodes. The top common conductor is designated the "A" conductor 121 and the lower conductor the "B" conductor 122. Electrode apparatus having three electrodes provide defibrillation and pace/sense functions via unipolar pace/sensing in which the conductive external housing of the implantable cardioverter/defibrillator itself is utilized as the pace/sense reference as opposed to a pace/sense electrode.

In summary, the catheter style electrode circuit embodiments disclosed herein, including the components disposed at the distal end of the catheters, eliminate the need for separate leads or conductors connected to each electrode of a standard four electrode catheter by solid state multiplexing at the distal end of the apparatus. Thus, electrical signals are combined and/or separated from at least two electrodes into the single lead. Thus, a three lead catheter is provided as shown in FIG. 3. Moreover, the electrode circuitry 65 and 92 shown in both FIGS. 4 and 5 eliminate the two separate conductors needed for the (defib+) and the (ps−) leads, hence reducing the total number of conductors to two and providing a two lead catheter. And, the circuitry 117 of FIG. 7 provides an electrode apparatus with two conductive leads connected to three electrodes for use in unipolar pace/sensing. It will be apparent to those skilled in the art that circuitry of the implantable defibrillator unit (not shown) functions to combine and or separate the combined electrode signals from each hybrid lead for further processing.

As many changes are possible to the embodiments of this invention utilizing the teachings thereof, the descriptions above, and the accompanying drawings should be interpreted in the illustrative and not the limited sense.

That which is claimed is:

1. An implantable defibrillation electrode apparatus, comprising:
   a. a body structure;
   b. a number "X", wherein X is at least 3, of electrode members disposed on said body structure for electrical communication with the exterior environment;
   c. a number "X—Y", wherein Y is a number between 1 and X—2, of conductive lead members, each lead member being communicatively connected to at least one electrode member and extending therefrom to a predetermined point on said body structure, and wherein each said electrode member is connected to at least one said lead member and at least one said lead member is connected to more than one said electrode member; and
   d. rectifier means connected between at least one lead member and at least one electrode member.

2. The defibrillation electrode apparatus of claim 1, wherein there are four electrode members and three lead members, a third lead member being connected to second and fourth electrode members, and first and second lead members each being connected to first and third electrode members, respectively.

3. The defibrillation electrode apparatus of claim 2, further comprising means to combine electrical signals at said third lead member from said second and fourth electrode members.

4. The defibrillation electrode apparatus of claim 1, wherein there are four electrode members and two lead members, a first lead member being connected to first and fourth electrode members, and a second lead member being connected to second and third electrode members.

5. The defibrillation electrode apparatus of claim 4, further comprising means to combine electrical signals at each said lead member from its respective connected electrode members.

6. The defibrillation electrode apparatus of claim 4, further comprising rectifier means connected between each said lead member and its respective said connections to said electrode members.

7. The defibrillation electrode apparatus of claim 1, wherein there are four electrode members, said electrode members including a positive defibrillation electrode, an negative defibrillation electrode, a positive pace/sense electrode and a negative pace/sense electrode, and wherein there are three lead members including including a first lead connected to said positive defibrillation lead, a second lead connected to said positive pace/sense electrode, and a third lead connected to said negative defibrillation lead and said positive pace/sense electrode, said apparatus further comprising firs rectifier means connected between said first lead and said negative defibrillation electorode, and second rectifier means connected between said first lead and said negative pace/sense electrode.

8. The defibrillation electrode apparatus of claim 7, wherein said first rectifier means is a zener diode having a cathode disposed toward said negative defibrillation electrode, and wherein said second rectifier mean comprises a function diode having an anode disposed toward is negative pace/sense electrode, and a resistor connected in parallel with respect to said junction diode.

9. The defibrillation electrode apparatus of claim 1, wherein there are four electrode members, said electrode members including a positive defibrillation electrode, an negative defibrillation electrode, a positive pace/sense electrode an a negative pace/sense electrode, and wherein there are two lead members including a first lead connected to said positive defibrillation electrode and to said negative pace/sense electrode, and a second lead connected to said negative defibrillation electrode and to said positive pace/sense electrode, said apparatus further comprising first rectifier mean connected between first lead and said positive defibrillation electrode, second rectifier means connected between said firs lead and said negative pace/sense electrode, third rectifier means connected between said second lead and said negative defibrillation electrode, and fourth rectifier means connected between said second lead and said positive pace/sense electrode.

10. The defibrillation electrode apparatus of claim 9, wherein said first rectifier means is a first diode having a cathode disposed toward said positive defibrillation electrode, said second rectifier comprises a second diode having an anode disposed toward said negative pace/sense electrode and a first resistor connected in parallel with respect to said second diode, said third rectifier means is a third diode having an anode disposed toward said negative defibrillation electrode, and wherein said fourth rectifier means comprises a fourth diode having a cathode disposed toward said positive pace/sense electrode and a second resistor connected in parallel with respect to said fourth diode.

11. The defibrillation electrode apparatus of claim 1, further comprising a first zener diode connected between said first lead a said positive defibrillation electrode, said first zener diode having a cathode disposed toward said positive defibrill electrode, first means to limit current connected between said second lead and said negative defibrillation electrode, a second zener diode connected between said second lead and said negative defibrillation electrode, said second zener diode having an anode disposed toward said negative defibrillator electrode, and second means to limit current connected said second lead and said positive pace/sense electrode.

12. The defibrillation electrode apparatus of claim 11, wherein said first and second zener diodes have a breakdown voltage of approximately 8 volts.

13. The defibrillation electrode apparatus of claim 11, wherein said first and second means to limit current each provide an effective resistance of approximately 200 ohms.

14. The defibrillation electrode apparatus of claim 13, wherein said first and said second means to limit current each comprise first and second field effect transistors having source, drain and gate electrodes, each said current limiting circuit further comprising a resistor connected between said source and drain electrodes of said first and second field effect transistors, said field effect transistor gate electrodes being connected on a far side of said resistor.

15. A, transvenous catheter-style defibrillation electrode apparatus, comprising:
   a. an elongated insulative body structure having a distal and a proximal end;
   b. four electrode members disposed on said body structure distal end for electrical communication with the human cardiac tissues, said four electrode members including a positive defibrillation electrode, a negative defibrillation electrode, a positive pace/sense electrode and a negative pace/sense electrode;

c. a first lead connected to said positive defibrillation lead, a second lead connected to said positive pace/sense electrode, and a third lead connected to said negative alefibrillation lead and to said positive pace/sense electrode, each lead extending from its respective said electrode to said proximal end of said body structure; and d. first rectifier means connected between said first lead and said negative defibrillation electrode, and second rectifier means connected between said first lead and said negative pace/sense electrode.

16. A, transvenous catheter-style defibrillation electrode apparatus, comprising:
   a. an elongated insulative body structure having a distal and a proximal end;
   b. four electrode members disposed on said body structure distal end for electrical communication with the human cardiac tissues, said four electrode members including a positive defibrillation electrode, a negative defibrillation electrode, a positive pace/sense electrode and a negative pace/sense electrode;
   c. a first lead connected to said positive defibrillation electrode and to said negative pace/sense electrode, and a second lead connected .to said negative defibrillation electrode and to said positive pace/sense electrode, each lead extending from its respective said electrode to said proximal end of said body structure; and
   d. first rectifier means connected between first lead and said positive defibrillation electrode, second rectifier means connected between said first lead and said negative pace/sense electrode, third rectifier means connected between said second lead and said negative defibrillation electrode, and fourth rectifier means connected between said second lead and said positive pace/sense electrodes.

17. A transvenous catheter-style defibrillation electrode apparatus, comprising:
   a. an elongated insulative body structure having a distal and a proximal end;
   b. four electrode members disposed on said body structure distal end for electrical communication with the human cardiac tissues, said four electrode members including a positive defibrillation electrode, a negative defibrillation electrode, a positive pace/sense electrode and a negative pace/sense electrode;
   c. a first lead connected to said positive defibrillation electrode and to said negative pace/sense electrode, and a second lead connected to said negative defibrillation electrode and to said positive pace/sense electrode, each lead extending from its respective said electrode to said proximal end of said body structure; and
   d. a first zener diode connected between said first lead and said positive defibrillation electrode, said first zener diode having a cathode disposed toward said positive defibrillation electrode, firs means to limit current connected between said second lad and said negative defibrillation electrode, a second zener diode connected between said second lead and said negative defibrillation electrode, said second zener diode having an anode disposed toward said negative defibrillation electrode, and second means to limit current connected between said second lead and said positive pace/sense electrode.

* * * * *